United States Patent [19]

Mikulski et al.

[11] Patent Number: 5,595,734
[45] Date of Patent: Jan. 21, 1997

[54] COMPOSITIONS COMPRISING ONCONASE (TM) AND LOVASTATIN

[75] Inventors: Stanislaw M. Mikulski, Essex Fells, N.J.; Wojciech J. Ardelt, New City, N.Y.

[73] Assignee: Alfacell Corporation, Bloomfield, N.J.

[21] Appl. No.: 921,619

[22] Filed: Jul. 28, 1992

Related U.S. Application Data

[63] Continuation-in-part of Ser. No. 436,141, Nov. 13, 1989, abandoned, which is a continuation-in-part of Ser. No. 178,118, Apr. 6, 1988, Pat. No. 4,882,421.

[51] Int. Cl.[6] .......................... A61K 37/54; C07K 14/00
[52] U.S. Cl. ........................................... 424/94.6; 530/350
[58] Field of Search .................. 424/94.6; 530/350; 549/292; 435/125; 560/256; 514/183, 12

[56] References Cited

U.S. PATENT DOCUMENTS 4,231,938  11/1980  Monaghan et al. ............... 549/292
4,882,421  11/1989  Shogen et al. ..................... 530/350
5,082,650  1/1992  Folkers et al. ..................... 424/10

OTHER PUBLICATIONS

Abstract, Dialog File 155 accessior No. 90291445 of Mikulski et al, May 1990. Cell Tissue Kinet. 23(3):237–246.

Abstract, Embase No. :92250984 of Mikulski et al. Aug. 1992, Br. J. Cancer. 66(2):304–310.

*Primary Examiner*—Robert A. Wax
*Assistant Examiner*—K. Cochrane Carlson

[57] ABSTRACT

A pharmaceutical known by the trademark ONCONASE, as described in pending commonly owned application application number 07/436,141 filed Nov. 13, 1989, is combined with two forms of another drug known as Lovastatin. The combination of ONCONASE with Lovastatin has unexpected bioactivity in vitro against ASPC-1 human pancreatic adenocarcinoma cells, A-549 human lung carcinoma cells and HT-520 human squamous cell lung carcinoma cells.

1 Claim, No Drawings

's 5,595,734

COMPOSITIONS COMPRISING ONCONASE (TM) AND LOVASTATIN

CROSS-REFERENCE TO RELATED APPLICATIONS

This application is a continuation-in-part of commonly-owned patent application of Ardelt, application number 07/436,141, filed Nov. 13, 1989, now abandoned, which is a continuation-in-part of commonly-owned application of Shogen et al., application number 07/178,118, filed Apr. 6, 1988 and now U.S. Pat. No. 4,882,421. The entire disclosures of these patent applications, including the drawings thereof, are hereby incorporated into this application by reference.

BACKGROUND OF THE INVENTION

The invention relates to pharmaceuticals, and more particularly relates to pharmaceuticals for use in treating cells which cause cancer tumors in humans.

The above-referenced patent application discloses a pharmaceutical which will be referred to herein by the trademark ONCONASE. It has now been determined that when this pharmaceutical is used in vitro in a combined therapy with two forms of another drug, the results of the combined therapy are, in certain instances, much more bioactive than would be expected.

This other drug is known as Lovastatin; the forms tested are the lactone form and the activated β-hydroxyacid form.

DETAILED DESCRIPTION OF PREFERRED EMBODIMENTS

In vitro data indicate that a combination of ONCONASE with a drug sold under the name Lovastatin is much more bioactive against human pancreatic ASPC-1 adenocarcinoma than would be expected, given the separate activities of ONCONASE and Lovastatin. In vitro data also indicate that a combination of ONCONASE with Lovastatin is much more bioactive against human lung A-549 carcinoma than would be expected, given the separate activities of ONCONASE and Lovastatin. In vitro data further indicate that a combination of ONCONASE with Lovastatin is much more bioactive against HT-520 human squamous cell lung carcinoma than would be expected, given the separate activities of ONCONASE and Lovastatin.

The preferred embodiment of the invention was tested using a cell culture assay. In such an assay, a cell line of known growth rate over a predetermined period is treated with the substance under test and the growth of the treated cells is compared with the growth which would ordinarily be expected from untreated cells.

ONCONASE, described in the above-referenced pending patent application and manufactured in accordance with the methodology described in U.S. Pat. No. 4,882,421 (which methodology is hereby incorporated herein by reference as if fully set forth herein) was dissolved in phosphate buffered saline (PBS) to obtain 1 mg/ml stock solution.

Lovastatin, which is available as a lactone from Merck, Sharp & Dohme (Rahway, N.J.), is

[1S-[1α(R*), 3α, 7β, 8β(2S*, 4S*), 8aβ]]-1, 2, 3, 7, 8, 8a -hexahydro-3, 7-dimethyl-8-[2-(tetrahydro-4-hydroxy-6-oxo -2H-pyran-2-yl)ethyl]-1-napthalenyl 2-methylbutanoate having an empirical formula of $C_{24}H_{36}O_5$ and a molecular weight of 404.55. The lactone form of Lovastatin, when activated by hydrolysis, is hydrolyzed to a β-hydroxyacid form.

The assay system utilized the ASPC-1 human pancreatic adenocarcinoma cell line and the A-549 human lung carcinoma cell line; both lines were obtained from the American Type Culture Collection (accession numbers were ATCC CRL 1682 for ASPC-1 and ATCC CCL 185 for A-549). Both cell lines were cultured in RPMI 1640 medium and supplemented with 20% (ASPC-1) or 10% (A-549) heat-inactivated fetal bovine serum and antibiotic-antimycotic solution composed of: 10,000 units per 1 ml penicillin, 10 mg per 1 ml streptomycin and 25 µg per 1 ml fungizone (complete growth medium). The assay system also used the HT-520 human squamous cell lung carcinoma line, which was obtained from the National Cancer Institute, Frederick Cancer Research Facility, Frederick, Md., with the kind permission of Dr. J. Minna. These cells were also grown in RPMI 1640 medium and also supplemented with 20% heat-inactivated fetal bovine serum, but were additionally supplemented with 1% glutamine and 1% Pen-Strep Fungizone.

The cells were seeded into 96-well tissue culture plates at a density of 2000 viable cells (50 µl per well) for the A-549 and HT-520 cell lines and 4000 viable cells (50 µl per well) for the ASPC-1 cell line. The cells were allowed to settle for 24 hours and then 50 µl of appropriate ONCONASE and/or Lovastatin (lactone form) or Lovastatin (β-hydroxyacid form) solutions were added per well. The following final concentrations were used:

a) ONCONASE, 100 ng to 10 µg/ml;

b) Lovastatin lactone, 15, 25 and 37 µM; and c) activated Lovastatin β-hydroxyacid, 15, 25 and 37 µM.

The plates were incubated for an additional six days at 37° C. and 5% carbon dioxide atmosphere. The total assay time was consequently seven days (one day in which the cells are allowed to settle, and six days of incubation). Percentages of viable cells were then determined using the MTT colorimetric assay using the Bio-Rad EIA microtiter plate reader.

The number of cells was determined by a direct count in an AO-Spencer "Brightline" hemocytometer with a Neubauer ruling. Attached cells were washed three times with Hanks' Balanced Salt Solution and treated with 2 ml of a 0.25% Trypsin—0.02% EDTA solution in buffered saline for about thirty seconds. The solution was removed and the cells were left at 37° C. for 10 minutes, then suspended in 10 ml of the complete growth medium. The 0.25 ml of the cell suspension was diluted with 0.75 ml of the complete growth medium and then 1 ml of 0.5% Trypan Blue solution was added and viable cells were counted.

Tables 1, 2 and 3 present the result of the above experiments. These tables are expressed in mean percent of growth inhibition, i.e. they indicate the effectiveness with which the tested therapies prevented the tested cancer cells from growing over the one week duration of the assay. Thus, a higher number indicates a higher bioactivity against the cell line used in the experiment.

TABLE 1

Mean % of growth inhibition for ASPC-1 human pancreatic carcinoma cells and $ED_{50}$ values for varying doses of ONCONASE alone and ONCONASE together with the lactone and activated β-hydroxyacid forms of Lovastatin

| ONCONASE Dose (µg/ml) | 0 | 0.1 | 1.0 | 10.0 | $ED_{50}$ |
|---|---|---|---|---|---|
| ONCONASE Alone | 0 | 19.7 | 12.6 | 76.4 | 7.561 |
| ONCONASE + 15 µM lactone | 12.4 | 25.7 | 59.8 | 99.4 | 0.282 |

TABLE 1-continued

Mean % of growth inhibition for ASPC-1 human pancreatic carcinoma cells and $ED_{50}$ values for varying doses of ONCONASE alone and ONCONASE together with the lactone and activated β-hydroxyacid forms of Lovastatin

| ONCONASE Dose (μg/ml) | 0 | 0.1 | 1.0 | 10.0 | $ED_{50}$ |
|---|---|---|---|---|---|
| ONCONASE + 15 μM β-hydroxyacid | 13.8 | 31.3 | 61.4 | 99.3 | 0.267 |
| ONCONASE + 25 μM lactone | 54.0 | 65.7 | 91.8 | 99.7 | 0.034 |
| ONCONASE + 25 μM β-hydroxyacid | 16.4 | 47.7 | 82.1 | 100.0 | 0.114 |
| ONCONASE + 37 μM lactone | 47.6 | 77.1 | 96.5 | 100.0 | 0.027 |
| ONCONASE + 37 μM β-hydroxyacid | 31.5 | 52.0 | 82.1 | 99.8 | 0.082 |

TABLE 2

Mean % of growth inhibition for A-549 human lung carcinoma cells and $ED_{50}$ values for varying doses of ONCONASE alone and ONCONASE together with the lactone and activated β-hydroxyacid forms of Lovastatin

| ONCONASE Dose (μg/ml) | 0 | 0.1 | 1.0 | 10.0 | $ED_{50}$ |
|---|---|---|---|---|---|
| ONCONASE Alone | 0 | 8.7 | 2.0 | 74.6 | 20.255 |
| ONCONASE + 15 μM lactone | 17.3 | 19.3 | 26.3 | 78.8 | 2.903 |
| ONCONASE + 15 μM β-hydroxyacid | 26.6 | 30.1 | 37.1 | 85.6 | 0.988 |
| ONCONASE + 25 μM lactone | 46.3 | 49.2 | 61.4 | 89.0 | 0.127 |
| ONCONASE + 25 μM β-hydroxyacid | 36.2 | 39.7 | 45.3 | 86.0 | 0.381 |
| ONCONASE + 37 μM lactone | 89.0 | 87.8 | 88.1 | 89.2 | <0.001 |
| ONCONASE + 37 μM β-hydroxyacid | 48.4 | 56.9 | 64.7 | 89.0 | 0.048 |

TABLE 3

Mean % of growth inhibition for HT-520 human squamous cell lung carcinoma cells and $ED_{50}$ values for varying doses of ONCONASE alone and ONCONASE together with the lactone and activated β-hydroxyacid forms of Lovastatin

| ONCONASE Dose (μg/ml) | 0 | 0.1 | 1.0 | 10.0 | $ED_{50}$ |
|---|---|---|---|---|---|
| ONCONASE Alone | 0 | 7.8 | 45.9 | 88.2 | 1.143 |
| ONCONASE + 15 μM lactone | 53.5 | 50.8 | 75.0 | 89.7 | 0.054 |
| ONCONASE + 15 μM β-hydroxyacid | 69.6 | 70.6 | 83.2 | 90.5 | 0.001 |
| ONCONASE + 25 μM lactone | 67.4 | 70.4 | 81.0 | 91.3 | 0.001 |
| ONCONASE + 25 μM β-hydroxyacid | 71.1 | 73.5 | 85.5 | 92.1 | 0.001 |
| ONCONASE + 37 μM lactone | 77.2 | 82.7 | 87.2 | 90.2 | <0.001 |
| ONCONASE + 37 μM β-hydroxyacid | 79.0 | 78.5 | 88.3 | 92.4 | <0.001 |

These results demonstrate that, in the instances shown, the bioactivities of ONCONASE combined with Lovastatin (both in the lactone form and in the activated β-hydroxyacid form) in the cases of ASPC-1 human pancreatic adenocarcinoma, A-549 human lung carcinoma and HT-520 human squamous cell lung carcinoma are much greater than would be expected from the bioactivities of the individual drugs alone. This may be seen from the $ED_{50}$ figures which are along the right edge of the Tables. These figures represent computed isoeffective doses; the figure shown is the amount of material which would be required to halve the growth rate of the cells undergoing the assay. Thus, the lower the $ED_{50}$ figure, the smaller the dose required to achieve the same bioactivity.

Chemical Analysis and Composition of ONCONASE

ONCONASE has been well characterized chemically. While ONCONASE is a protein isolated from rana pipiens, it is believed that ONCONASE may be produced using genetic engineering techniques, as long as the end result has the following chemistry and structure:

ONCONASE is a pure protein (i.e. homogeneous, as established by standard tests which are used to assay the proteins). By electrophoresis, the molecular weight of ONCONASE is approximately 14,500 Daltons. Calculation of the molecular weight based upon the below listed amino acid sequence indicates that the molecular weight should be 11,819 Daltons. However, because metal ions may have bonded to the protein despite all efforts to remove them, and because different isotopes may be involved, the molecular weight of ONCONASE as determined by mass spectroscopy is 12,430 Daltons. In view of this discrepancy, the molecular weight of ONCONASE as determined by mass spectrometry will be considered to be approximately 12,000 Daltons. ONCONASE has an isoelectric point pI which is at least 9.5 and may be as high as 10.5. ONCONASE has a blocked amino terminal group and is essentially free of carbohydrates (as determined by anthrone and orcinol methods).

ONCONASE has the following amino acid composition:

| Amino Acid Analysis | |
|---|---|
| AMINO ACID RESIDUE | MOL % (24 HOUR ACID HYDROLYSIS) |
| Aspartic acid/Asparagine | 13.39 |
| Threonine | 9.84 (Note 1) |
| Serine | 8.08 (Note 1) |
| Glutamic acid/Glutamine | 5.88 |
| Proline | 3.98 |
| Glycine | 2.98 |
| Alanine | 2.92 |
| Cystine/2 | 7.77 |
| Valine | 7.77 |
| Methionine | 0.94 |
| Isoleucine | 5.29 (Note 2) |
| Leucine | 4.95 |
| Tyrosine | 2.85 |
| Phenylalanine | 5.73 |
| Histidine | 2.99 |
| Lysine | 11.78 |
| Arginine | 2.85 |
| Tryptophan | Not Determined (Note 3) |
| Approximate Total | 99.99% |

Note 1: Threonine and serine are partially destroyed during hydrolysis and this value is corrected for such partial destruction.
Note 2: This value is corrected for incomplete hydrolysis.
Note 3: Tryptophan cannot be detected in acid hydrolysis of proteins because it is destroyed and is consequently shown as Not Determined. However, analysis of the ultraviolet spectrum revealed the presence of one tryptophan residue per molecule.

| Amino Acid Composition (as calculated from amino acid sequence) | |
| --- | --- |
| AMINO ACID | NUMBER OF RESIDUES PER MOLECULE OF MATERIAL |
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Approximate Total | 104 |

ONCONASE has been sequenced. As is shown below, the total length of the sequence is 104 residues. The N-terminus of the protein is pyroglutamic acid (<Glu). This is a cyclized derivative of glutamic acid which is devoid of the free amino group necessary for direct sequencing and which therefore "blocks" the N-terminus of the protein.

When the shorter fragment described in U.S. Pat. No. 4,882,421 was cleaved with pyroglutamate aminopeptidase, pyroglutamic acid was removed from the shorter fragment, permitting sequencing to commence at the second residue. Such cleavage is a strong indication that the N-terminus is pyroglutamic acid since pyroglutamate aminopeptidase only cleaves pyroglutamic acid. The presence of pyroglutamic acid was further confirmed by mass spectrometry of the referenced shorter fragment. The molecular weight of this shorter fragment determined by mass spectrometry agreed well with the weight as calculated assuming that pyroglutamic acid was present and disagreed with the weight as calculated assuming that glutamic acid was present.

ONCONASE has the following amino acid sequence:

```
  1    2    3    4    5    6    7    8    9   10
<Glu—Asp—Trp—Leu—Thr—Phe—Gln—Lys—Lys—His—

11                                          20
Ile—Thr—Asn—Thr—Arg—Asp—Val—Asp—Cys—Asp—

21                                          30
Asn—Ile—Met—Ser—Thr—Asn—Leu—Phe—His—Cys—

31                                          40
Lys—Asp—Lys—Asn—Thr—Phe—Ile—Tyr—Ser—Arg—

41                                          50
Pro—Glu—Pro—Val—Lys—Ala—Ile—Cys—Lys—Gly—

51                                          60
Ile—Ile—Ala—Ser—Lys—Asn—Val—Leu—Thr—Thr—

61                                          70
Ser—Glu—Phe—Tyr—Leu—Ser—Asp—Cys—Asn—Val—

71                                          80
Thr—Ser—Arg—Pro—Cys—Lys—Tyr—Lys—Leu—Lys—

81                                          90
Lys—Ser—Thr—Asn—Lys—Phe—Cys—Val—Thr—Cys—

91                                         100
Glu—Asn—Gln—Ala—Pro—Val—His—Phe—Val—Gly—

101        104
Val—Gly—Ser—Cys
```

Although a preferred embodiment has been described above, the scope of the invention is limited only by the following claims:

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: N ( i v ) ANTI-SENSE: N ( v ) FRAGMENT TYPE: N-terminal ( v i ) ORIGINAL SOURCE:
        ( A ) ORGANISM: Rana pipiens
        ( D ) DEVELOPMENTAL STAGE: Embryo ( x i ) SEQUENCE DESCRIPTION: SEQ ID NO:1:

Glu Asp Trp Leu Thr Phe Gln Lys Lys His Ile Thr Asn Thr Arg Asp

-continued

| 1 | | | | 5 | | | | | 10 | | | | | 15 |
|---|---|---|---|---|---|---|---|---|---|---|---|---|---|---|
| Val | Asp | Cys | Asp<br>20 | Asn | Ile | Met | Ser | Thr<br>25 | Asn | Leu | Phe | His | Cys<br>30 | Lys | Asp |
| Lys | Asn | Thr<br>35 | Phe | Ile | Tyr | Ser | Arg<br>40 | Pro | Glu | Pro | Val | Lys<br>45 | Ala | Ile | Cys |
| Lys | Gly<br>50 | Ile | Ile | Ala | Ser | Lys<br>55 | Asn | Val | Leu | Thr | Thr<br>60 | Ser | Glu | Phe | Tyr |
| Leu<br>65 | Ser | Asp | Cys | Asn | Val<br>70 | Thr | Ser | Arg | Pro | Cys<br>75 | Lys | Tyr | Lys | Leu | Lys<br>80 |
| Lys | Ser | Thr | Asn | Lys<br>85 | Phe | Cys | Val | Thr | Cys<br>90 | Glu | Asn | Gln | Ala | Pro<br>95 | Val |
| His | Phe | Val | Gly<br>100 | Val | Gly | Ser | Cys |

We claim:

1. A bioactive pharmaceutical comprising a protein having the following amino acid sequence:

```
1   2   3   4   5   6   7   8   9   10
<Glu—Asp—Trp—Leu—Thr—Phe—Gln—Lys—Lys—His—

11                                          20
Ile—Thr—Asn—Thr—Arg—Asp—Val—Asp—Cys—Asp—

21                                          30
Asn—Ile—Met—Ser—Thr—Asn—Leu—Phe—His—Cys—

31                                          40
Lys—Asp—Lys—Asn—Thr—Phe—Ile—Tyr—Ser—Arg—

41                                          50
Pro—Glu—Pro—Val—Lys—Ala—Ile—Cys—Lys—Gly—

51                                          60
Ile—Ile—Ala—Ser—Lys—Asn—Val—Leu—Thr—Thr—

61                                          70
Ser—Glu—Phe—Tyr—Leu—Ser—Asp—Cys—Asn—Val—

71                                          80
Thr—Ser—Arg—Pro—Cys—Lys—Tyr—Lys—Leu—Lys—

81                                          90
Lys—Ser—Thr—Asn—Lys—Phe—Cys—Val—Thr—Cys—

91                                          100
Glu—Asn—Gln—Ala—Pro—Val—His—Phe—Val—Gly—

101         104
Val—Gly—Ser—Cys
``` and

[1S-[1α(R*), 3α, 7β, 8β(2S*, 4S*), 8aβ]]-1, 2, 3, 7, 8, 8a-hexahydro -3,7-dimethyl-8-[2-(tetrahydro-4-hydroxy-6-oxo-2H-pyran-2-yl)ethyl]-1-napthalenyl 2-methylbutanoate.

* * * * *